United States Patent
Forsryd et al.

(10) Patent No.: US 11,896,775 B2
(45) Date of Patent: Feb. 13, 2024

(54) CATHETER AND PROCESS FOR MANUFACTURING A CATHETER

(71) Applicant: Automationspartner i Helsingborg AB, Ramlösa (SE)

(72) Inventors: Gustav Joakim Forsryd, Klippan (SE); Lars Rune Bertil Paulsson, Gantofta (SE)

(73) Assignee: Automationspartner i Helsinborg AB, Ramlösa (SE)

( * ) Notice: Subject to any disclaimer, the term of this patent is extended or adjusted under 35 U.S.C. 154(b) by 229 days.

(21) Appl. No.: 17/676,539

(22) Filed: Feb. 21, 2022

(65) Prior Publication Data
US 2022/0265960 A1   Aug. 25, 2022

(30) Foreign Application Priority Data
Feb. 22, 2021   (EP) .................................... 21158534

(51) Int. Cl.
*A61M 25/00* (2006.01)
*B26F 1/00* (2006.01)

(52) U.S. Cl.
CPC ....... *A61M 25/0015* (2013.01); *B26F 1/0015* (2013.01)

(58) Field of Classification Search
CPC .......................... A61M 25/0015; B26F 1/0015
USPC ............................................................ 83/30
See application file for complete search history.

(56) References Cited

U.S. PATENT DOCUMENTS

| | | | | |
|---|---|---|---|---|
| 2,972,779 A | * | 2/1961 | Cowley | B26F 1/0015 493/287 |
| 4,554,849 A | * | 11/1985 | Benham | B26F 1/02 83/40 |
| 8,475,699 B2 | * | 7/2013 | Triel | A61M 25/0015 264/319 |
| 8,679,091 B2 | | 3/2014 | Morris et al. | |
| 9,084,867 B2 | * | 7/2015 | Triel | B29C 45/261 |
| 9,186,480 B2 | * | 11/2015 | Olsen | A61M 25/0017 |
| 9,440,051 B2 | * | 9/2016 | Gyrn | A61B 5/150564 |
| 10,874,841 B2 | * | 12/2020 | Johnson | A61M 37/0069 |
| 10,898,643 B2 | * | 1/2021 | Gyrn | A61M 5/14248 |
| 2006/0027063 A1 | * | 2/2006 | Currier | A61M 25/0015 83/13 |

(Continued)

FOREIGN PATENT DOCUMENTS

EP   0861143 A1   9/1998
EP   2129424 B1   5/2015
(Continued)

*Primary Examiner* — Omar Flores Sanchez
(74) *Attorney, Agent, or Firm* — KUSNER & JAFFE

(57) ABSTRACT

The present invention relates to a catheter and a process for manufacturing a radially extending opening in tubing for a catheter. The tubing having at least one lumen being enclosed by at least one tubing wall and the process comprises placing tubing in a fixture, applying force to the tubing and thereby fixing the tubing in the fixture in a position for making an opening, pressing a heated depression tool against the surface of the tubing creating a depression area in the at least one tubing wall, and punching an opening cutting tool through the at least one tubing wall within the depression area creating an opening in the depression area of the at least one tubing wall, the opening extending from the exterior of the tubing to the lumen of the tubing.

20 Claims, 6 Drawing Sheets

(56) References Cited

U.S. PATENT DOCUMENTS

2014/0013907 A1\* 1/2014 Kalbacher ............ B26F 1/0015
                                                                 83/660

FOREIGN PATENT DOCUMENTS

| | | |
|---|---|---|
| EP | 2944345 A1 | 11/2015 |
| EP | 3698839 A1 | 8/2020 |
| GB | 1580924 A | 12/1980 |
| WO | WO1981/03614 | 12/1981 |
| WO | WO1997/18067 A1 | 5/1997 |
| WO | WO2001/93935 A1 | 12/2001 |
| WO | WO2008/155145 A1 | 12/2008 |
| WO | WO2010/070048 A1 | 6/2010 |

\* cited by examiner

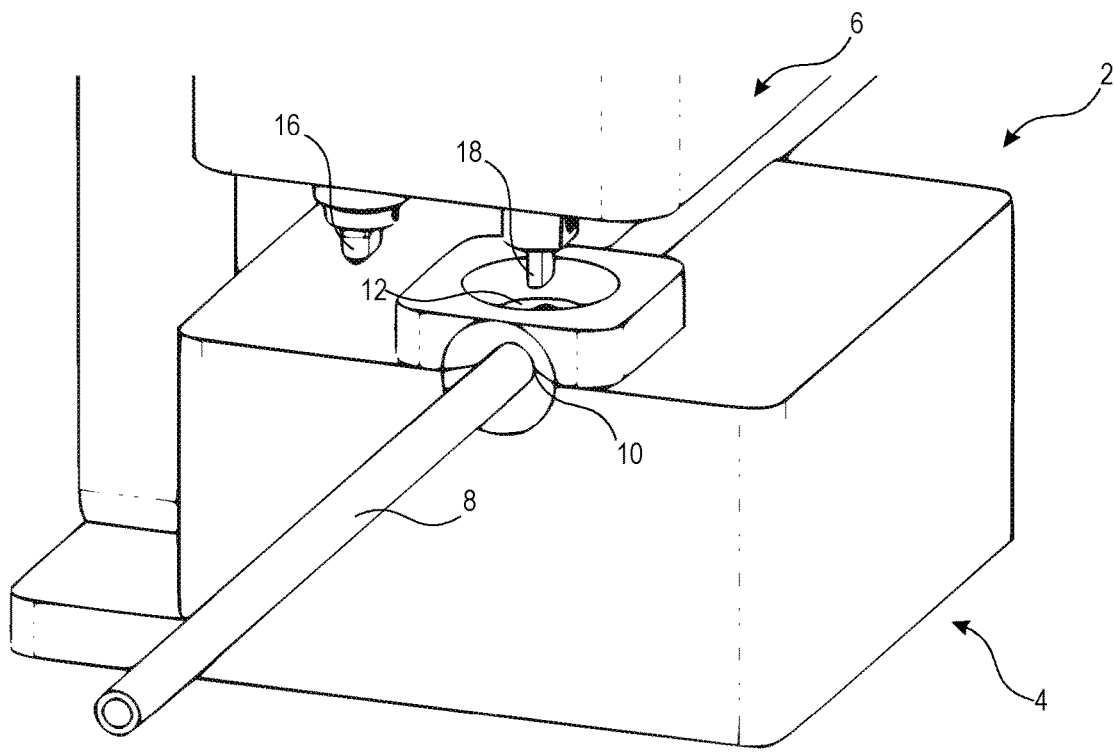
FIG. 1
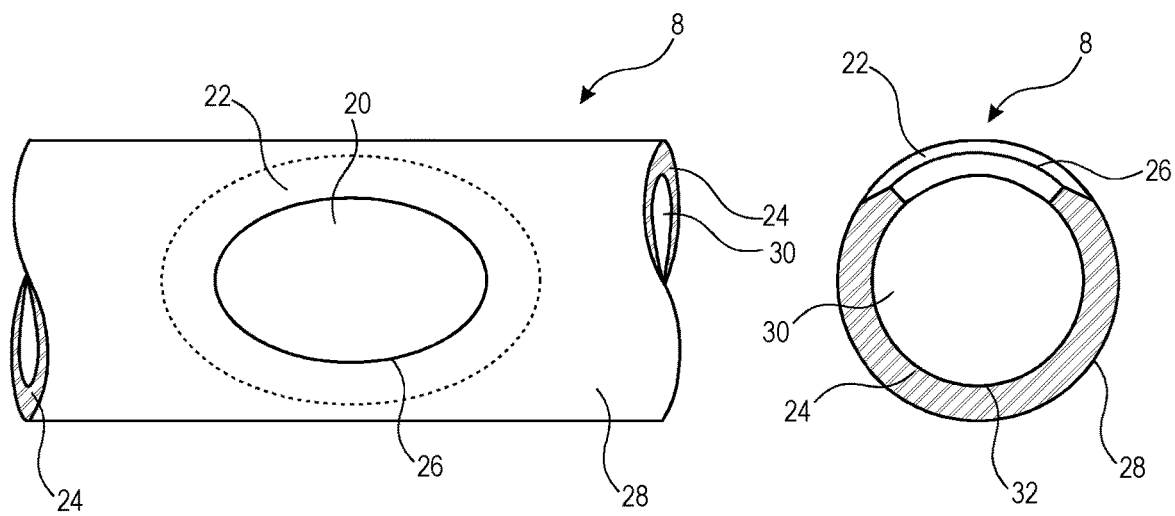
FIG. 2a  FIG. 2b

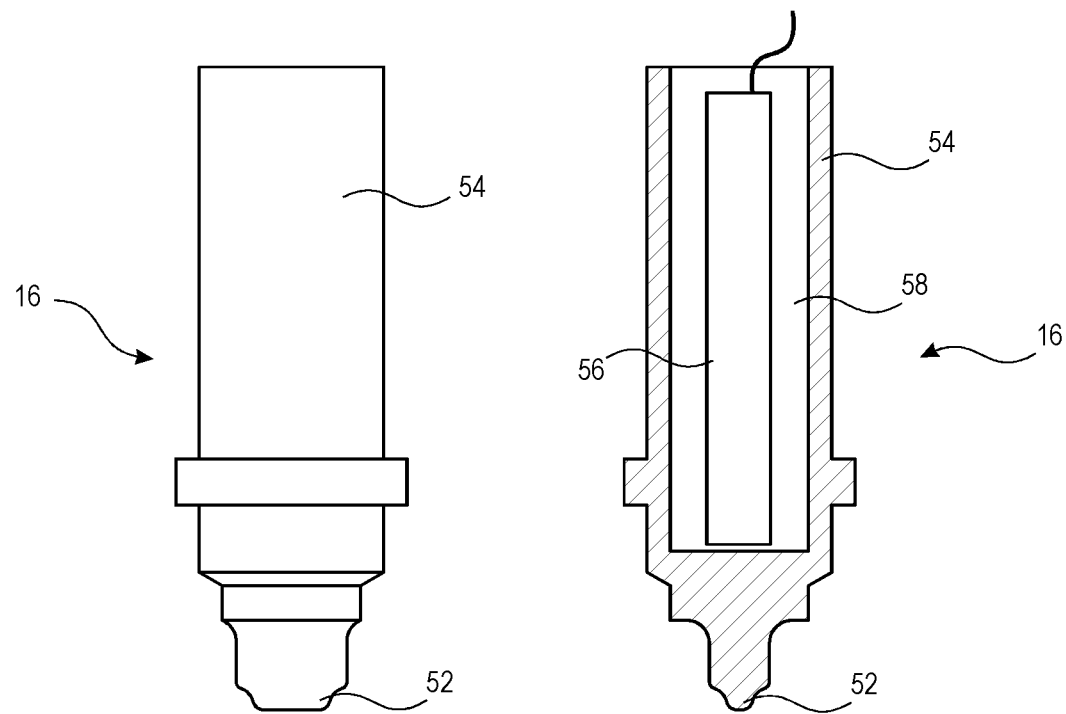
FIG. 5a  FIG. 5b
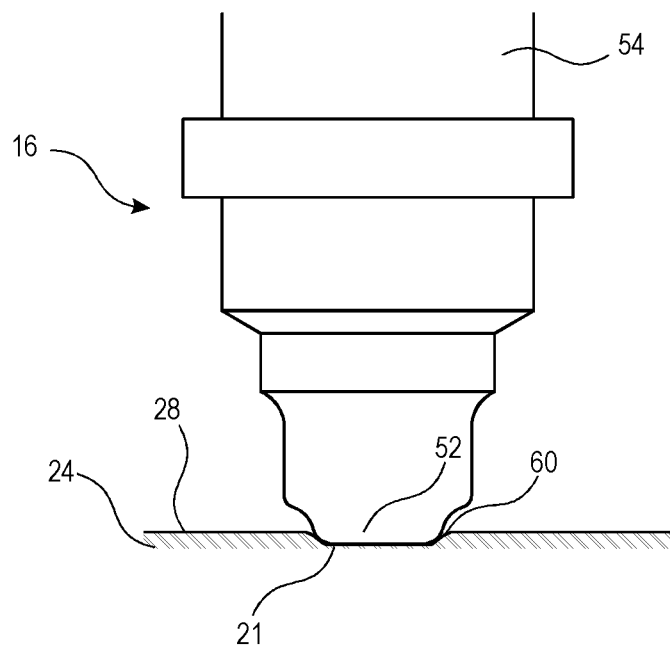
FIG. 6

CATHETER AND PROCESS FOR MANUFACTURING A CATHETER

TECHNICAL FIELD

The present invention relates to processes for manufacturing a catheter and more specifically for manufacturing radially extending openings in tubing for a catheter. Further, the present invention relates to a catheter manufactured according to the process.

BACKGROUND

Catheters for insertion into human or animal bodies may include openings arranged to make the exterior to the catheter communicate with the lumen of the catheter, for example, for drainage, medication, exploration, dilation, and the like. Such catheters are often inserted into and/or through passages of the body, e.g. the urinary tract, the stomach, a lung, a blood vessel, the rectum, the urethra and ureter, and in such procedures it is important that the catheter does not have any sharp edges or sharp protrusions resulting in discomfort for the user or patient or, even worse, risking inflicting damage to the body. This problem has previously been identified and various solutions have been presented over the years.

In the U.S. Pat. No. 2,972,779 a process is described for making plastic tubing having smooth holes for catheters. Holes punched in the catheters described in the patent are rough and result in unnecessary pain, irritation, or injuries when inserted into a patient. The patent teaches that these problems may be avoided by punching the hole and then grinding the area of the tubing having the punched hole with an emery wheel carrying a solvent for the tubing. The patent also teaches another way to produce the smooth holes by punching and molding the holes in the catheter using a metallic die acting as an electrode leading high frequency voltage to another electrode inserted into the tubing and heating the area for the punching of the hole. The wall of the tubing is sufficiently liquified or melted so that the material will flow during the punching operation. The punching die is smoothly curved to the bottom of the die in order to remove sharp edges in the punching process.

In the European patent application EP 2 129 424 a method for rounding the edge of an opening in a tubular body of an intermittent catheter is shown. The document describes the pushing of a heated mandrel into an eyelet, being an opening in the wall of the tubular body, and having the mandrel deform an external edge of the eyelet forming rounded edges.

SUMMARY OF THE INVENTION

One object of the present invention is to provide an alternative process for manufacturing radially extending openings in tubing for a catheter.

The invention is defined by the appended independent claims. Additional features and advantages of the concepts disclosed herein are set forth in the description which follows, and in part will be obvious from the description, or may be learned by practice of the described technologies. The features and advantages of the concepts may be realized and obtained by means of the instruments and combinations particularly pointed out in the appended claims. These and other features of the described technologies will become more fully apparent from the following description and appended claims or may be learned by the practice of the disclosed concepts as set forth herein.

In a first aspect a process for manufacturing radially extending openings in tubing for a catheter, the tubing having at least one lumen being enclosed by at least one tubing wall, the process comprises placing tubing in a fixture, applying force to the tubing and thereby fixing the tubing in the fixture in a position for making an opening, pressing a heated depression tool against the surface of the tubing creating a depression area in the at least one tubing wall, and punching an opening cutting tool through the at least one tubing wall within the depression area creating an opening in the depression area of the at least one tubing wall, the opening extending from the exterior of the tubing to the lumen of the tubing. One advantage of making a depression in the tubing wall before punching the opening is that the process of making the opening is facilitated. This results from the fact that lesser precision, compared with the prior art, is required in the combination of operations for achieving an opening in the tubing that is not harming the body that the tubing is inserted into. For instance, even if the opening is cut somewhat of center in a depression area the edges of the opening may be below a level of the tubing outer surface. Further, the production becomes more reliable and results in improved quality. Moreover, this process also results in a decreased risk of discomfort or harm for users or patients that have to use or be treated using a catheter.

In some embodiments the area of the depression area may be 10%-40% larger than the area of the opening or the area may be 25%-35% larger than the area of the opening. In some other embodiments the area of the depression area may be 10%-90% larger than the area of the opening or the depression area may be 55%-75% larger than the area of the opening. The advantages being that the requirement for the precision of the opening cutting may be less restricted.

In yet some embodiments the processing step of applying force to the tubing includes the applying of the force to the tubing so that inner surface areas of the tubing wall facing each other are in physical contact with each other. One advantage of applying such a force to the tubing may be that during the process step of punching the depression and the opening the portion of the tubing where the depression and opening is to be made is more rigid and less resilient for the forces applied in the punching of the depression and the opening, respectively. Moreover, there are no need for introducing a supportive structure into the tubing to make the tubing rigid in order to provide suitable rigidity and support for performing the depression operation and cutting operation, respectively.

According to some embodiments the process step of punching the opening cutting tool through the at least one tubing wall further comprises punching the opening cutting tool through the at least one tubing wall within the depression area into the area of the tubing wall facing the area of the tubing where the opening is cut. The cutting into the opposing wall like this may be advantageous in that the likelihood of the cutting operation successfully cut through the entire wall at the site for the opening and not leaving any strands retaining a cutout portion in place may increase.

According to yet some embodiments the processing step of applying a force to at least a portion of the tubing temporarily flattens the tubing at least during the steps of pressing and punching. One advantage of applying such a force to the tubing may be that during the process step of punching the depression and the opening the portion of the tubing where the depression and opening is to be made is more rigid and less resilient for the forces applied in the punching of the depression and the opening, respectively. Moreover, there are no need for introducing a supportive structure into the tubing to make the tubing rigid in order to provide suitable rigidity and support for performing the depression operation and cutting operation.

In some embodiments the process further comprises relaxing the force to the at least one portion of the tubing and releasing the tubing from the fixed position, moving the tubing in the fixture, applying force to the tubing, and thereby fixing the tubing in a position for making a second opening and then repeating the processing steps of pressing the heated depression tool against the surface of the tubing and punching the opening cutting tool through the at least one tubing wall. In this way the process may be used for manufacturing additional openings in the tubing.

Moreover, in some embodiments the tubing may have a circular cross section and the opening punched by the cutting tool may extend radially from the exterior of the tubing to the lumen of the tubing.

According to some embodiments the temperature of the heated depression tool is below the melting point of the material in the tubing wall. An advantage of this may be that the transition from the tubing surface to the indentation of the depression becomes smooth. The effect may even be such that the surface of the tubing is stretched into the depression and thereby forming part of the transition to the depression area even without even having the depression tool being in contact with that portion of the area. The temperature of the heated depression tool may according to some embodiments be in the range of 100-180° C.

According to another aspect of the invention a catheter is produced using any embodiment of the process described above. The advantages presented to a feature above is relevant for the feature in this aspect as well.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description. Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a sensor" or "the sensor" may include several sensors, and the like. Furthermore, the word "comprising" does not exclude other elements or steps.

BRIEF DESCRIPTION OF THE DRAWINGS

In order to best describe the manner in which the above-described embodiments are implemented, as well as define other advantages and features of the disclosure, a more specific description is provided below and is illustrated in the appended drawings. Understanding that these drawings depict only exemplary embodiments of the invention and are not therefore to be considered to be limiting in scope, the examples will be described and explained with additional specificity and detail through the use of the accompanying drawings in which:

FIG. 1 depicts a schematic view of a machine for manufacturing openings in tubing according to some embodiments of the invention, FIG. 2a show a portion of a tubing where an opening according to some embodiments of the invention has been made, FIG. 2b shows a section view of the portion of the tubing in FIG. 2a, FIG. 3 shows a flowchart of a process of manufacturing an opening in tubing according to some embodiments of the invention, FIG. 5a shows a view of a depression tool according to some embodiments of the invention, FIG. 5b shows a section view of the depression tool of FIG. 5a, and FIG. 6 shows the depression tool of FIG. 5a-b in position of making a depression in the tubing.

Further, in the figures like reference characters designate like or corresponding parts throughout the several figures.

DETAILED DESCRIPTION OF THE INVENTION

Figure 3:
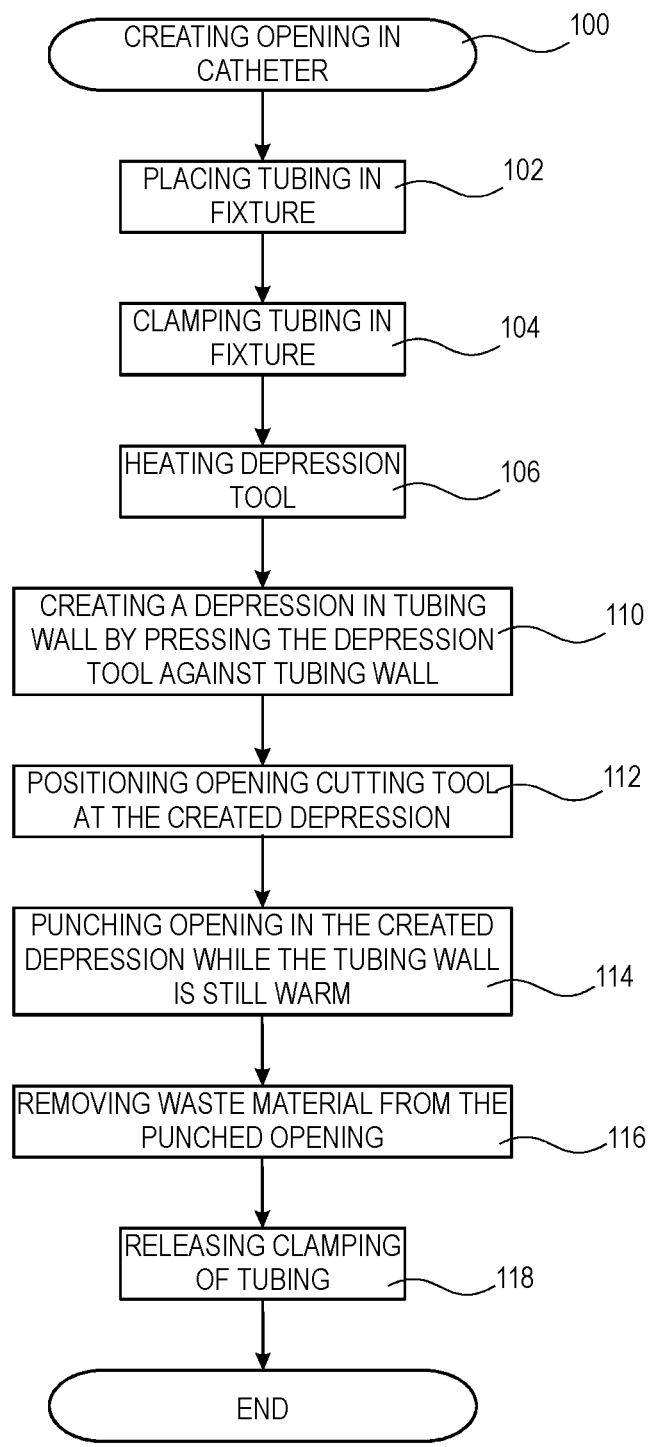

Hereinafter, certain embodiments will be described more fully with reference to the accompanying drawings. It will be apparent to those skilled in the art that various modifications and variations can be made without departing from the inventive concept. Other embodiments will be apparent to those skilled in the art from consideration of the specification and practice disclosed herein. The embodiments herein are provided by way of example so that this disclosure will be thorough and complete, and will fully convey the scope of the inventive concept, and that the claims be construed as encompassing all equivalents of the present inventive concept which are apparent to those skilled in the art to which the inventive concept pertains. If nothing else is stated, different embodiments may be combined with each other.

Now referring to FIG. 1, showing parts of a machine 2 arranged for making openings in tubing 8 during a process of manufacturing of a catheter according to some embodiments of the invention. The machine 2 includes a fixture 4 and a tool carrier 6. The fixture 4 is designed and configured to receive and fix the tubing 8 during the operation of making an opening in the tubing 8 and includes a tubing receiving opening 10 for receiving the tubing 8 in the fixture 4, a punching opening 12 arranged substantially perpendicular to an insertion direction of the tubing receiving opening 10 for allowing physical access to the tubing 8 inserted in the fixture 4 and allowing punching of an opening in the tubing 8. Further, the fixture 4 includes a clamping arrangement 14, showed in FIGS. 4a-f, for fixing the tubing 8 in the fixture 4. The tool carrier 6 includes a depression tool 16, may also be referred to as a depression punch 16, and a cutting tool 18, may also be referred to as a cutting punch 18, each is arranged to enable alternating access via the punching opening 12 to a wall of the tubing 8 inserted in the machine.

The tubing to be provided with openings according to the invention may be any flexible tubing suitable for manufacturing of catheters. The tubing may be flexible to such a degree allowing the catheter when inserted into the body of a patient to be pliant enough to easily be inserted via a non-straight path. The tubing should at least be pliable enough to follow a path having a bend with a radius that a rigid tubing would not be able to follow easily. In some embodiments the tubing material may have a hardness of 40-90 Shore A, in some embodiments the hardness may be 60-90 Shore A. Shore A hardness according to the standard DIN EN ISO 868. The tubing may for example be made of polymer materials such as thermoplastic elastomers (TPE), Polyurethanes (PUR), Polyvinyl chlorides (PVC), and/or Fluorinated Ethylene Propylene (FEP). In the example tubing shown in this description as being processed into a catheter is presented as single-lumen tubing. However, the invention may be applied to multi-lumen tubing or to co-extruded tubing as well.

In FIGS. 2a-b an example of a portion of a tubing 8 provided with an opening 20 according to embodiments of the invention is depicted. An opening 20 is cut in a depression area 22 in the tubing wall 24 after making the depression forming the depression area. Thereby minimizing the risk of any sharp edges from the edge 26 of the opening 20 resulting in pain, irritation, or injuries when inserted into a patient. This is an effect of the opening being cut in the depression area 22 and thereby a possible sharp and harmful edge 26 will be positioned below the outer surface 28 of the tubing 8 and thereby minimizing the risk of scratching or tearing when the tubing is used as a catheter and is inserted into a patient. The opening 20 is extending from the exterior of the tubing to a lumen 30 of the tubing 8 for allowing passage of fluid, gas, or similar matter from an area at the opening into the tubing or from the tubing into an area at the opening. The opening may be in the shape of a circle, an oval, an elongated rounded shape, an elongated rounded shape having sharp connections at the shorter end, i.e. somewhat eye shaped, etc.

In the example of FIGS. 2a-b the tubing 8 is formed having a circular cross section and the opening 20 is cut radially through the wall 24 of the tubing 8. The outer diameter of the cross section of the tubing 8 may vary depending on the application, e.g. from 0.1 mm in outer diameter to more than 10 mm in outer diameter.

Now referring to FIG. 3 and FIGS. 4a-f, depicting a flowchart of a process 100 for manufacturing openings 20 in a catheter tubing 8, e.g. openings 20 such as the one described in connection with FIGS. 2a-b. Some of the steps are also showed in FIGS. 4a-f where positioning of the tools 16,18 and the tubing 8 at instances in the process are depicted. The tubing 8 to be provided with openings is placed in the fixture, step 102, by, for example, inserting it into the fixture via the tubing receiving opening, see FIG. 4a. When the tubing 8 is in the desired position for making the opening 20, the clamping arrangement 14 is engaged and the tubing 8 is fixed in the fixture, step 104. In the embodiment shown in FIG. 4b the process step of clamping by driving a rigid body 14 towards the piping and a surface in which the punching opening 12 is arranged and thereby applying a force to the tubing and elastically deforming the tubing 8 into a squeezed shape, see FIG. 4b, in the portion of the tubing 8 where the opening 20 is to be cut.

Figure 4A:
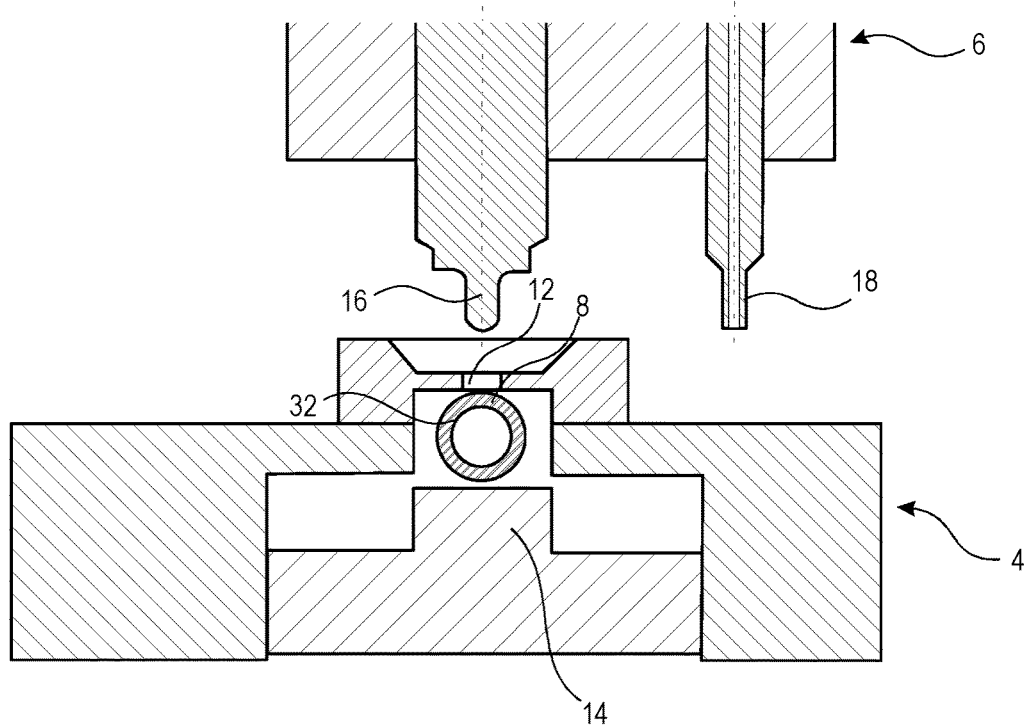
FIG. 4a-4f shows schematic views of a machine for manufacturing openings in tubing according to some embodiments of the invention when in position for performing various steps of a process for manufacturing an opening in tubing according to some embodiments of the invention.
Figure 4B:
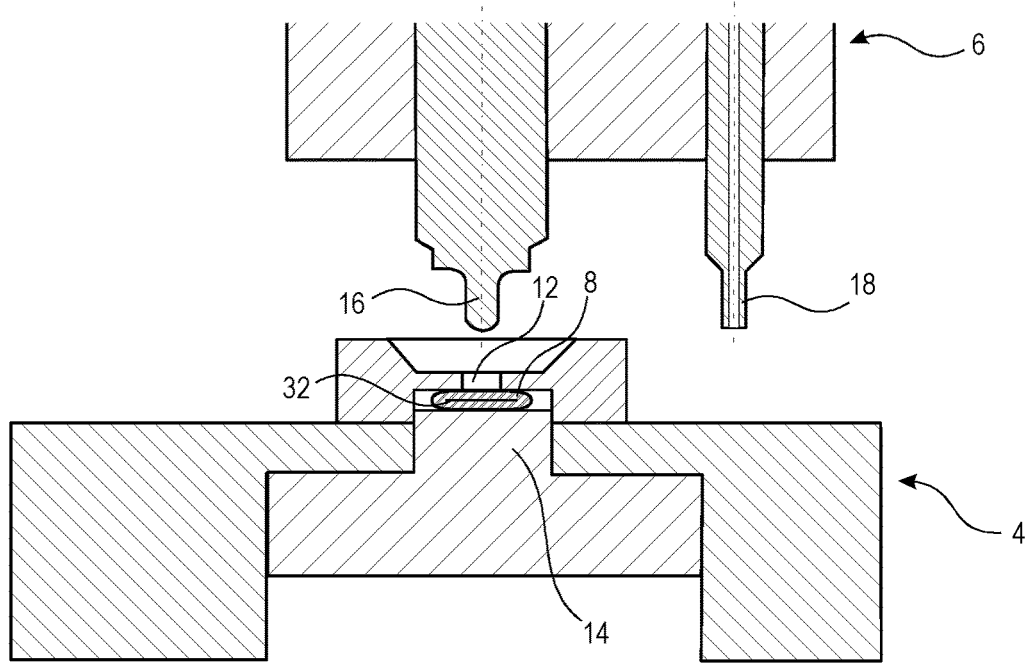

The force applied to the tubing 8 by the clamping assembly 14 may be of such force as required for fixing it in position for the operations in connection with making the opening 20, i.e. not necessarily flattening the tube as shown in FIG. 4b. Accordingly, in some embodiments the force applied is only to such degree that the friction between the tubing and the clamping assembly 14 is keeping the tubing 8 fixed, thereby minimizing the risk of deforming the tubing 8. In some embodiments the force applied by the clamping assembly 14 is of such force that in addition to the tubing 8 being fixed the tubing 8 is flattened, which in some applications is facilitating the making of the opening 20. In yet other embodiments the force applied by the clamping assembly 14 may be of such force that the inner surface 32 of the tubing wall at the side of the tubing where the opening 20 is to be made comes in contact with the inner surface 32 opposite to the side where the opening is to be made. In these later embodiments the making of the opening 20 is further facilitated, in particular for pliable tubing.

When the tubing 8 is sufficiently clamped or during the clamping of the tubing 8, the depression tool 16 is heated, step 106. The depression tool 16 is in some embodiments heated to a temperature range of 100-180° C. The temperature of the depression tool is dependent on the material of the tubing and should be high enough to make a permanent depression 21 when the depression tool is pushed into the tubing wall 24 and less than the melting temperature of the tubing material. Alternatively, the depression tool is kept heated continuously during processing of a plurality of openings 20.

Figure 4C:
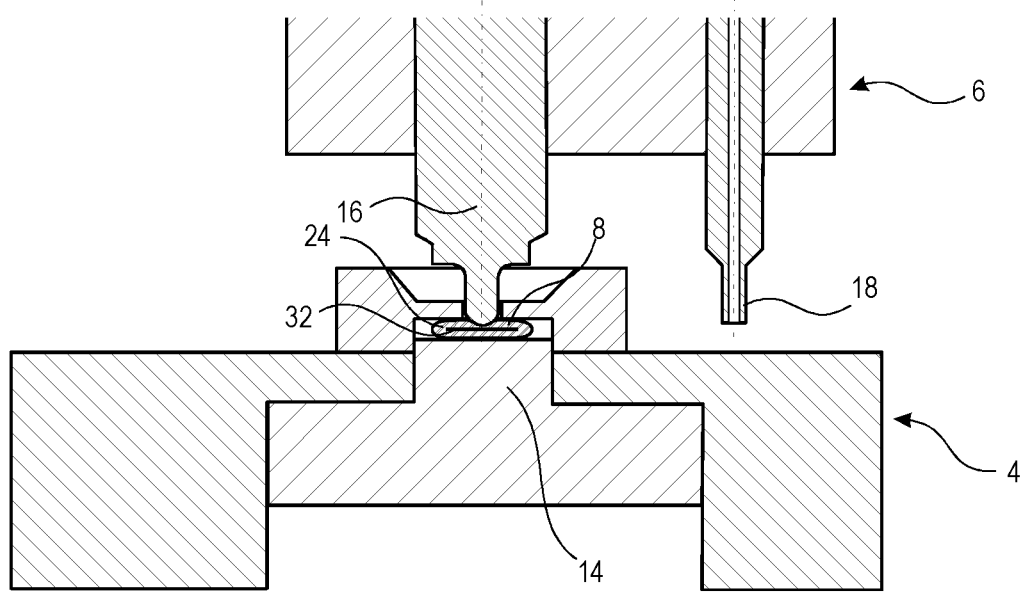
Figure 4D:
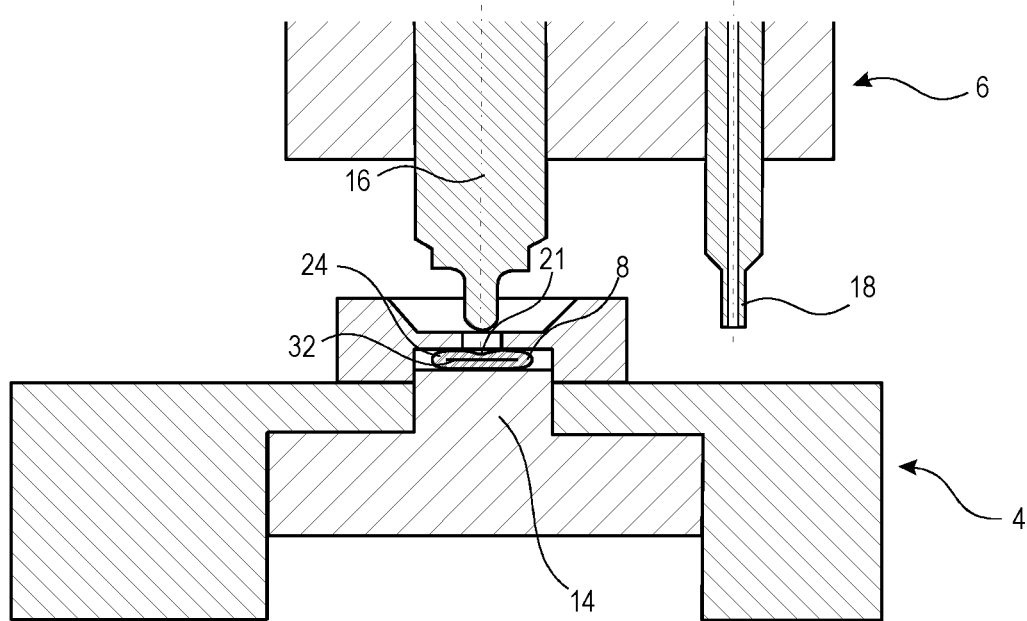

The heated depression tool 16 is, as depicted in FIG. 4c, pressed into the tubing wall 24, creating the depression 21 in the tubing wall 24, step 110. When the depression tool 16 is retracted from the tubing wall 24 the permanent depression 21 is left on the tubing 8, see FIG. 4d. The area of the depression 21 is in the present description referred to as the depression area 22.

Figure 4E:
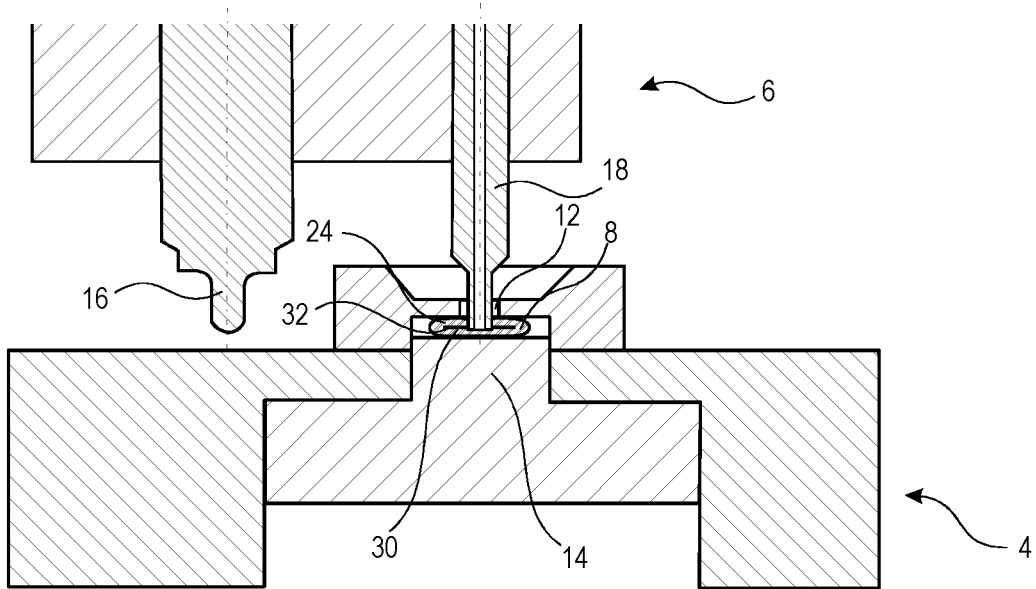

Then the cutting tool 18 is moved into position at the punching opening 12 and the created depression before the tubing has cooled down, step 112. When in position, the cutting tool 18 is punched through the tubing wall 24 into the lumen 30, step 114. The cutting tool punching through the tubing wall 24 is depicted in FIG. 4e. The cutting tool 18 is, in some embodiments, punched through the tubing wall 24 into the lumen and partially into the tubing inner surface 32 opposite to the wall area where the opening 20 is created. One advantage of the depression area 22 and thereby the area where the cutting tool 18 is punched through the tubing wall 24 being warm is that there is less loose particles and other debris generated by the cutting. Accordingly, the risk of residue material from the cutting being present in the tubing decreases. The tubing wall being warm during cutting also results in a smoother cutting surface.

Figure 4F:
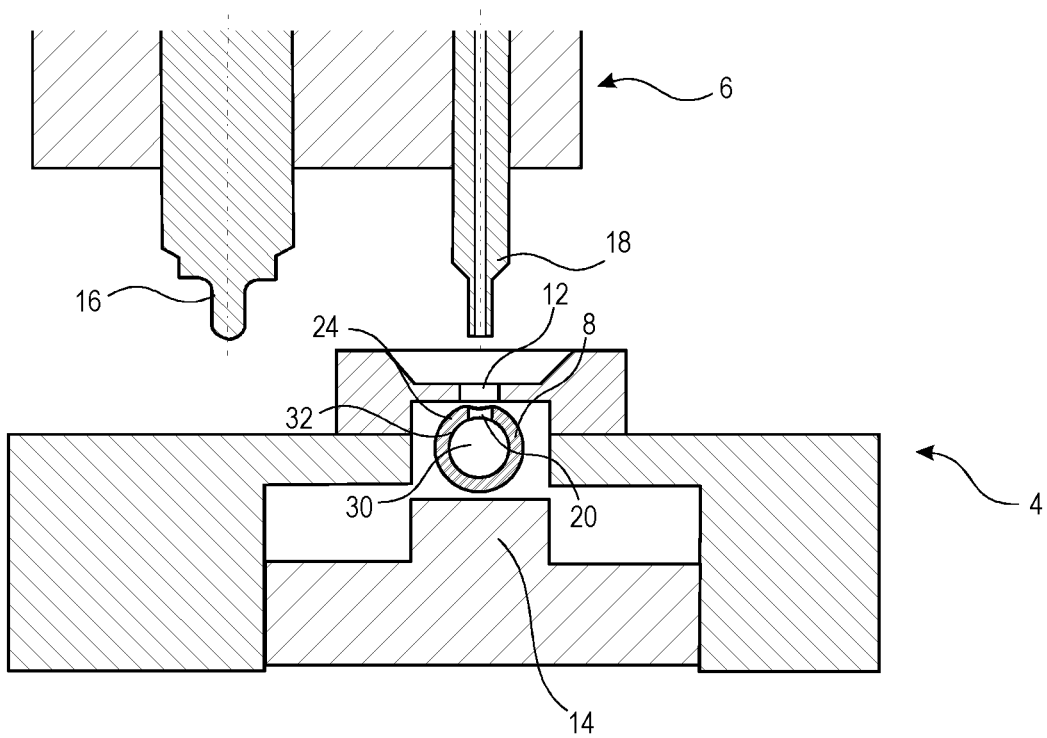

Then the cutting tool 18 is retracted and the waste material from the cutting of the opening, i.e. the solid piece of material that is cut out to form the opening 20, is removed, step 116, and the clamping of the tubing is released, step 118, see also FIG. 4f.

The process may then start over again in order to make another opening 20 at another portion of the same tubing 8 or in another tubing.

Now referring to FIGS. 5a-b, an example depression tool 16 according to some embodiments is shown. The depression tool 16 may be manufactured from any heat conducting material being non-deformable under the temperatures and pressures used to make the depression in the tubing wall 24. Metals such as alumina, iron, steel etc. may be used in the depression tool 16. The surface of the depression tool, at least the surface/surfaces that are to make the depression, may be coated with a non-stick coating. The depression tool 16 has a depression head 52 and a shaft 54. The depression head 52 is the part that is pressed into the tubing wall 24 for making the depression, as shown in FIG. 6, and the shaft 54 is connecting the depression head 52 to the tool carrier 6. Further, the depression tool 16 may include a heating device 56, e.g. a heating device 56 arranged in a cavity 58 of the shaft 54, a coil wrapped around the shaft 56, etc. Yet another alternative is to have the heating generated by a heater 56 in the tool carrier 6 and then have the heat conducted via the shaft 54 to the depression head 52. According to some embodiments the depression head 52 is formed as half a spherocylinder that is cut along the long axis of the geometry arranged so that the convex surface faces away from the tool and being arranged to be pushed into the tubing wall 24 to make the depression. A spherocylinder is to be understood as a form that is made up of two hemispheres connected by a cylinder.

In FIG. 6 a depression head 52 according to some embodiments is shown pressed into the tubing wall 24. In some embodiments of the process the temperature of the depression tool is of such value that the tubing wall 24 is deformed into the depression 24 and that some surface material not directly touched by the depression head 52 is bending down into the depression 21 creating a smooth transition 60 from outer surface 28 of the tubing into the depression 21. The transition may also be described as having a very large radius.

In some embodiments the area of the depression area 22 is substantially 90% larger than the area of the opening 20. In some embodiments the depression area 22 is 10%-90% larger than the area of the opening 20. In some embodiments the area of the depression area 22 is 10%-40% larger than the area of the opening 20. In some embodiments the depression area 22 is substantially 30% larger than the opening 20. One advantage from some of the embodiments where the depression area 22 is made before the opening 20 is cut and having a larger area than the opening is that the punching of the opening may be facilitated as the precision in the positioning of the cutting tool 18 within the depression area does not have to be exactly in the center of the depression area 22 as long as the edge of the opening 20 is positioned at within the depression area 22 at a position lower than the outer surface 28 of the tubing 8 to such a degree that the edge of the opening 20 do not come in contact with tissue of a patient when inserted into the patient (human or animal) during normal operation. The expression lower position than the outer surface 28, or below the outer surface 28, used above should be understood as a position at a distance from the outer surface 28 in the direction of the lumen 30 of the tubing 8. The entire depression area 22 represent such position as it is depressed into the tubing wall 24, but only a subset of positions in the depression are at an acceptable distance from the outer surface 28 of the tubing 8.

The various embodiments described above are provided by way of illustration only and should not be construed to limit the invention. For example, the principles herein may be applied to any remotely controlled device. Those skilled in the art will readily recognize various modifications and changes that may be made to the present invention without following the example embodiments and applications illustrated and described herein, and without departing from the scope of the present disclosure.

What is claimed:

1. A process for manufacturing a radially extending opening in tubing for a catheter, the tubing having at least one lumen being enclosed by at least one tubing wall, the process comprising:
   placing tubing in a fixture,
   applying force to the tubing and thereby fixing the tubing in the fixture in a position for making an opening,
   pressing a heated depression tool against the surface of the tubing creating a depression area in the at least one tubing wall, and
   punching an opening cutting tool through the at least one tubing wall within the depression area creating an opening in the depression area of the at least one tubing wall, the opening extending from the exterior of the tubing to the lumen of the tubing.

2. The process of claim 1, wherein the area of the depression area is 10%-40% larger than the area of the opening.

3. The process of claim 1, wherein the area of the depression area is 25%-35% larger than the area of the opening.

4. The process of claim 1, wherein the area of the depression area is 10%-90% larger than the area of the opening.

5. The process of claim 1, wherein the area of the depression area is 55%-75% larger than the area of the opening.

6. The process of claim 1, wherein the processing step of applying force to the tubing includes the applying of the force to the tubing so that inner surface areas of the tubing wall facing each other are in physical contact with each other.

7. The process of claim 6, wherein the process step of punching the opening cutting tool through the at least one tubing wall further comprises punching the opening cutting tool through the at least one tubing wall within the depression area into the area of the tubing wall facing the area of the tubing where the opening is cut.

8. The process of claim 1, wherein the processing step of applying a force to at least a portion of the tubing temporarily flattens the tubing at least during the steps of pressing and punching.

9. The process of claim 1, further comprising:
   relaxing the force to the at least one portion of the tubing and releasing the tubing from the fixed position,
   moving the tubing in the fixture,
   applying force to the tubing and thereby fixing the tubing in a position for making a second opening and then repeating the processing steps of pressing the heated depression tool against the surface of the tubing and punching the opening cutting tool through the at least one tubing wall.

10. The process of claim 1, wherein the tubing has a circular cross section and the opening punched by the cutting tool extends radially from the exterior of the tubing to the lumen of the tubing.

11. The process of claim 1, wherein the temperature of the heated depression tool is below the melting point of the material in the tubing wall.

12. The process of claim 1, wherein the temperature of the heated depression tool is in the range of 100-180° C.

13. A catheter comprising tubing having at least one lumen being enclosed by at least one tubing wall and having at least one radially extending opening through the at least one tubing wall, wherein the at least one radially extending opening in the tubing is obtained by the process of:
   placing tubing in a fixture,
   applying force to the tubing and thereby fixing the tubing in the fixture in a position for making an opening,
   pressing a heated depression tool against the surface of the tubing creating a depression area in the at least one tubing wall, and
   punching an opening cutting tool through the at least one tubing wall within the depression area creating an opening in the depression area of the at least one tubing wall, the opening extending from the exterior of the tubing to the lumen of the tubing.

14. The catheter of claim 13, wherein the area of the depression area is 10%-40% larger than the area of the opening.

15. The catheter of claim 13, wherein the area of the depression area is 25%-35% larger than the area of the opening.

16. The catheter of claim 13, wherein the area of the depression area is 10%-90% larger than the area of the opening.

17. The catheter of claim 13, wherein the area of the depression area is 55%-75% larger than the area of the opening.

18. The catheter of claim 13, wherein the process step of punching the opening cutting tool through the at least one tubing wall further comprises punching the opening cutting tool through the at least one tubing wall within the depression area into the area of the tubing wall facing the area of the tubing where the opening is cut.

19. The catheter of claim 13, wherein the tubing has a circular cross section and the opening punched by the cutting tool extends radially from the exterior of the tubing to the lumen of the tubing.

20. The catheter of claim 13, wherein the temperature of the heated depression tool is below the melting point of the material in the tubing wall.

\* \* \* \* \*